(12) United States Patent
Nadeau

(10) Patent No.: US 10,765,550 B2
(45) Date of Patent: Sep. 8, 2020

(54) APPARATUS FOR FIXING BAD POSTURE

(71) Applicant: Sheena Jean Nadeau, San Francisco, CA (US)

(72) Inventor: Sheena Jean Nadeau, San Francisco, CA (US)

(*) Notice: Subject to any disclaimer, the term of this patent is extended or adjusted under 35 U.S.C. 154(b) by 498 days.

(21) Appl. No.: 15/595,703

(22) Filed: May 15, 2017

(65) Prior Publication Data
US 2017/0325988 A1 Nov. 16, 2017

Related U.S. Application Data

(60) Provisional application No. 62/336,281, filed on May 13, 2016.

(51) Int. Cl.
*A61F 5/02* (2006.01)

(52) U.S. Cl.
CPC .............. *A61F 5/024* (2013.01); *A61F 5/026* (2013.01); *A61F 5/028* (2013.01)

(58) Field of Classification Search
CPC .......... A61F 5/0106; A61F 5/02; A61F 5/024; A61F 5/026; A61F 5/028; A61F 5/05; A61F 5/058; A61F 5/05841; A61F 5/0585

USPC .............................................. 602/19, 23, 26
See application file for complete search history.

(56) References Cited

U.S. PATENT DOCUMENTS

| 5,127,897 A * | 7/1992 | Roller ..................... A61F 5/024 |
| | | 128/107.1 |
| 5,868,691 A * | 2/1999 | Vishnevsky ............ A61F 5/026 |
| | | 128/845 |

* cited by examiner

*Primary Examiner* — Keri J Nelson

(57) ABSTRACT

An apparatus for fixing bad posture includes a support rod, multiple length-adjustable straps, and multiple strap-attachment points. The apparatus for fixing bad posture prevents the user from slouching by affixing the support rod to the user's back with the straps. The support rod is a rigid member that is placed against a user's back. The support rod has a rod body, a mounting face, and a bracing face. The rod body is the structural component of the support rod. The bracing face and mounting face are positioned on opposite lateral surfaces of the rod body. Thus positioned, the bracing face is pressed against the user's back when correcting posture. The strap-attachment points are connection mechanisms for the length-adjustable straps that are distributed along the length of the support rod. As such, each of the length-adjustable straps is attached to the support rod by a corresponding strap-attachment point.

3 Claims, 8 Drawing Sheets

's back to encourage the user to maintain an erect carriage. The support rod 1 comprises a rod body 11, a mounting face 12, and a bracing face 13. Each of the plurality of length-adjustable straps 2 is a strap that is used to affix the support rod 1 to the back of the user. Additionally, each length-adjustable strap 2 can be, but is not limited to, a belt, a rope, or a bungie cord. The rod body 11 is the structural foundation of the rod that maintains the rod's overall shape. Additionally, the mounting face 12 and the bracing face 13 are laterally positioned along the rod body 11. Moreover, the mounting face 12 and the bracing face 13 are positioned opposite to each other about the rod body 11. Consequently, the bracing face 13 is a lateral surface of the support rod 1 that forces the user to maintain good posture by being pressed against the user's back. The mounting face 12 is the lateral surface of the support rod 1 on which various fasteners can be mounted. The plurality of strap-attachment points 3 is a collection of location where the plurality of length-adjustable straps 2 can be attached to the support rod 1. As such, the plurality of strap-attachment points 3 is distributed along the rod body 11. Additionally, each of the plurality of length-adjustable straps 2 is engaged to a corresponding point 31 from a plurality of selected points 32, wherein the plurality of selected points 32 is from the plurality of strap-attachment points 3. As a result, each of the plurality of length-adjustable straps 2 is maintained in a position that is proximal to a specific location of the user's body by one of the plurality of strap-attachment points 3.

APPARATUS FOR FIXING BAD POSTURE

The current application claims a priority to the U.S. Provisional Patent application Ser. No. 62/336,281 filed on May 13, 2016. The current application is filed on May 15, 2017 while May 13, 2016 was on a weekend.

FIELD OF THE INVENTION

The present invention relates generally to a physical therapy device. More specifically, the present invention relates to a support bar and strapping system that, when attached to the user's back, corrects the user's posture by preventing the user from slouching.

BACKGROUND OF THE INVENTION

Obtaining good posture is a very difficult endeavor for some individuals. It is physically taxing to maintain an erect carriage while sitting and standing. Another factor that contributes to bad posture is the reality of modern life. In contemporary society, people are frequently sitting in chairs for extended periods of time. This encourages slouching, because slouching in a chair is often the most comfortable way to sit in a chair.

The present invention, the apparatus for fixing bad posture, addresses the issue of slouching posture by preventing a user from slouching. This is accomplished by strapping a rod onto the user's back. The straps of the rod are placed at various positions along the user's body to prevent the user from slouching.

For example, the plurality of length-adjustable straps 2 could include three straps: a first strap that is intended to secure the support rod 1 to the user's forehead; a second strap that is intended to secure the support rod 1 to the user's chest; and a third strap that is intended to secure the support rod 1 to the user's waist. Each of these straps is attached to the support rod 1 at a corresponding point 31 that facilitates securing the strap to the appropriate body part.

The present invention further comprises a padding material 14 that is used to minimize discomfort while the user is wearing the present invention. The padding material 14 is superimposed onto the bracing face 13 so that the padding material 14 is positioned between the support rod 1 and the user's back.

Figure 1:
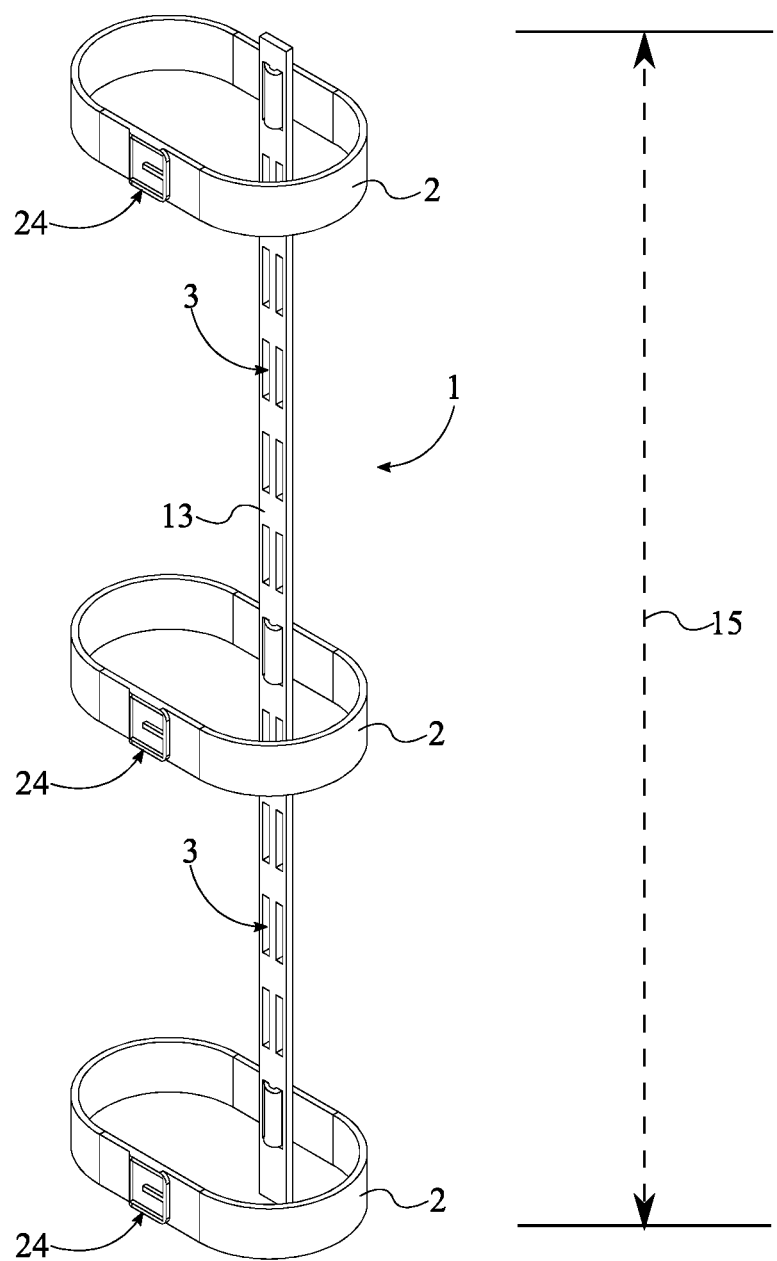
FIG. 1 is a perspective view of the preferred embodiment of the present invention.
Figure 3:
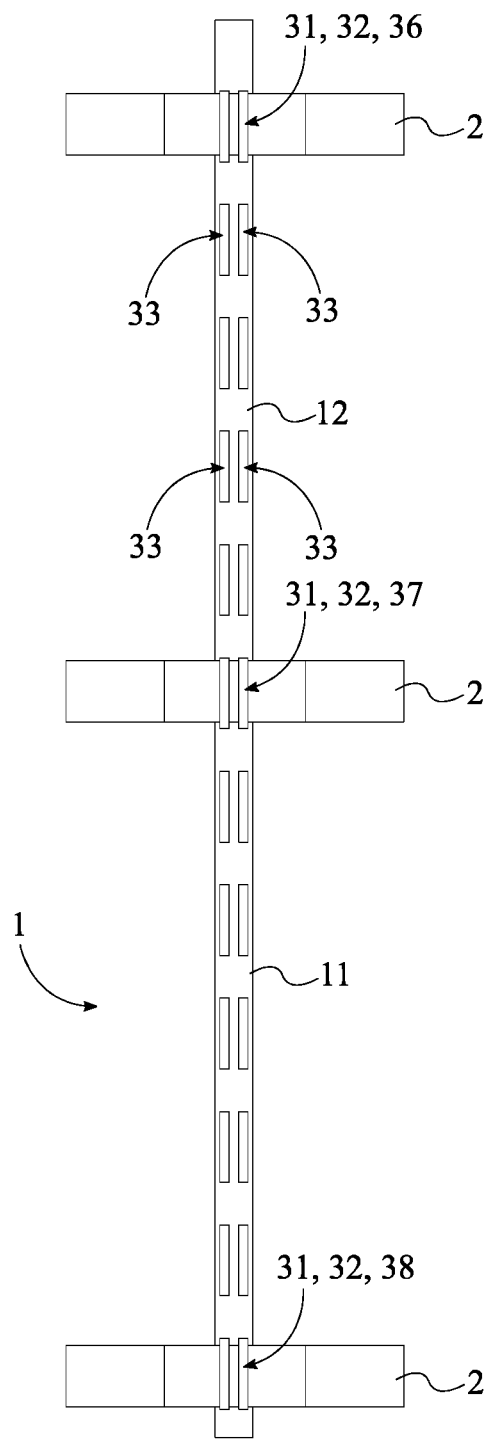
FIG. 3 is a rear view of the present invention.
Figure 4:
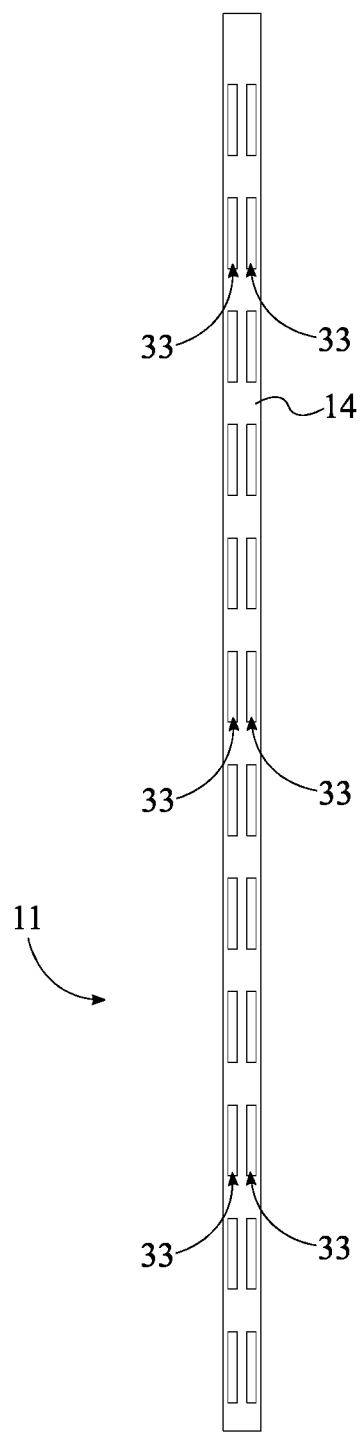
FIG. 4 is a front view of the present invention with the plurality of length-adjustable straps removed.

As can be seen in FIG. 1 and FIG. 3, each of the plurality of strap-attachment points 3 is positioned to enable the user to mount the plurality of length-adjustable straps 2 in locations that facilitate straightening the user's posture. To that end, the plurality of strap-attachment points 3 is serially distributed along the strap body. Thus distributed, the plurality of strap-attachment points 3 gives the user multiple points to attach the plurality of length-adjustable straps 2 along the length of the spine. In the preferred embodiment of the present invention, each of the plurality of strap-attachment points 3 comprises a pair of slots 33. The pair of slots 33 is two slots that are used to slidably engage a single length-adjustable strap. Each of the pair of slots 33 traverses through the rod body 11 from the mounting face 12 to the bracing face 13. Additionally, the pair of slots 33 is positioned offset from each other. Finally, the pair of slots 33 is oriented parallel to a length 15 of the support rod 1. Accordingly, the pair of slots 33 forms channels that enable the plurality of length-adjustable straps 2 to pass through the support rod 1. Specifically, each of plurality of length-adjustable straps 2 traverses through each of the pair of slots 33 of the corresponding point 31. Consequently, each of the length-adjustable straps 2 is able to pass through the pair of slots 33 and become slidably engaged to the corresponding point 31. Furthermore, the positioning and orientation of the

DETAIL DESCRIPTIONS OF THE INVENTION

All illustrations of the drawings are for the purpose of describing selected versions of the present invention and are not intended to limit the scope of the present invention.

As can be seen in FIG. 1 through FIG. 6, the present invention, the apparatus for fixing bad posture, is a posture correction system that prevents a user from slouching. The present invention trains the user to maintain good posture by attaching a rod to the user's back. The rod is strapped to the user's body at locations that prevent the user from slouching. To accomplish this, the present invention comprises a support rod 1, a plurality of length-adjustable straps 2, and a plurality of strap-attachment points 3. The support rod 1 is preferably a rigid structure that is pressed against the user pair of slots 33 facilitates passing the plurality of length-adjustable straps 2 through the pair of slots 33 when affixing the present invention to the user's body.

Figure 2:
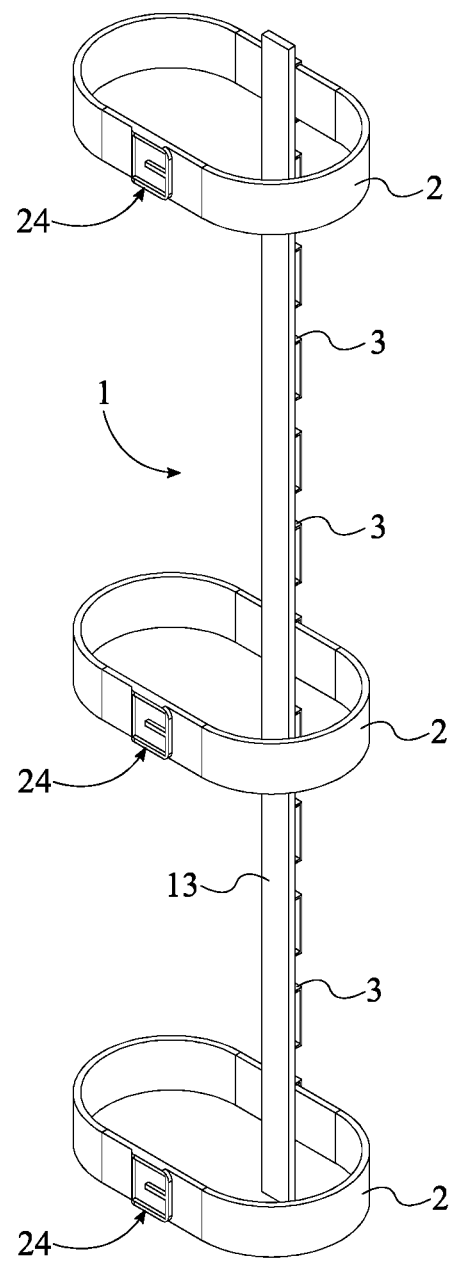
FIG. 2 is a perspective view of a first alternative embodiment of the present invention.
Figure 5:
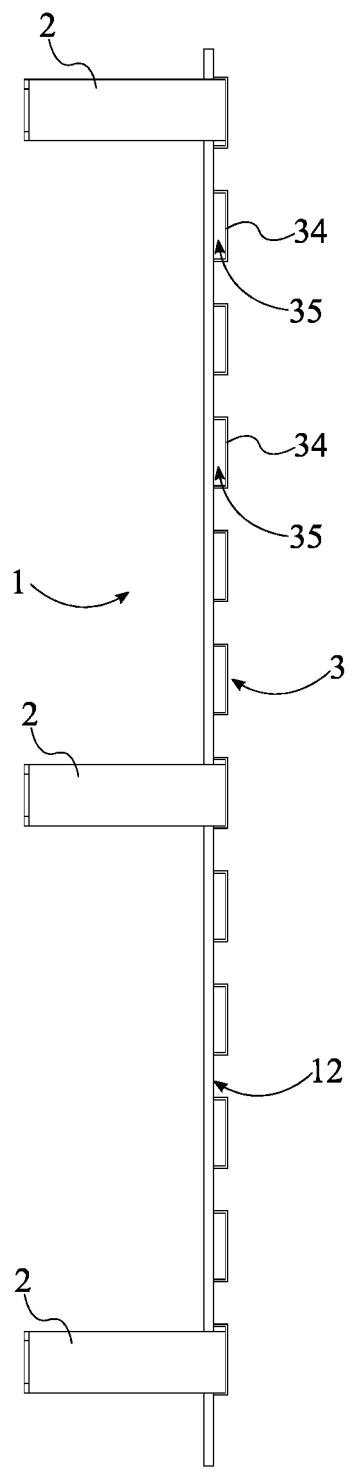
FIG. 5 is a left-side view of the second alternative embodiment of the present invention.

As can be seen in FIG. 1, FIG. 2, and FIG. 5, in a second alternative embodiment of the present invention, the plurality of strap-attachment points 3 is made up of a plurality of loops that are connected to the mounting face 12 of the support rod 1 Each of the plurality of loops can be, but is not limited to, a D-ring or an eyelet. In the second alternative embodiment, each of the plurality of strap-attachment points 3 comprises a loop body 34 and a loop hole 35. The loop body 34 is the structural foundation for each of the plurality of strap-attachment points 3. Additionally, the loop body 34 is tangentially connected to the mounting face 12 so that only one side of the loop body 34 is attached to the support rod 1 to maintain the loop body 34 in a position that facilitates engaging the plurality of length-adjustable straps 2. The loop hole 35 is peripherally delineated by the loop body 34. Consequently, the loop hole 35 is an opening that traverses through the loop body 34. Furthermore, the loop hole 35 is oriented perpendicular to the length 15 of the support rod 1. Thus positioned, the plurality of length-adjustable straps 2 is not impeded when passing through the loop hole 35. Specifically, each of plurality of length-adjustable straps 2 traverses through the loop hole 35 of the corresponding point 31. Accordingly, each of the length-adjustable straps 2 is able to pass through the loop hole 35 and become slidably engaged to the corresponding point 31.

As can be seen in FIG. 1 and FIG. 3, as described above, the present invention is able to function as a posture correction device by using the plurality of length-adjustable straps 2 to attach the support rod 1 to various locations on the user's body. To accomplish this, each of the plurality of length-adjustable straps 2 is attached to the support rod 1 at a corresponding point 31 that is close to a specific body part. As such, the plurality of selected points 32 comprises a head-proximal point 36, a chest-proximal point 37, and a waist-proximal point 38. The chest-proximal point 37 is positioned offset from the head-proximal point 36 along the support rod 1. Additionally, the waist-proximal point 38 is positioned offset from the chest-proximal point 37 along the support rod 1, opposite to the head-proximal point 36. Consequently, the head-proximal point 36, the chest-proximal point 37, and the waist-proximal point 38 are located close to the area of the user's body that the plurality of length-adjustable straps 2 will wrap around. Specifically, the head-proximal point 36 is positioned to facilitate attaching the support rod 1 to the user's head by wrapping a single length-adjustable strap 2 around the user's forehead. Similarly, the chest-proximal point 37 is positioned to facilitate attaching the support rod 1 to the user's chest by wrapping a single length-adjustable strap 2 around the user's chest. Likewise, the waist-proximal point 38 is positioned to facilitate attaching the support rod 1 to the user's waist by wrapping a single length-adjustable strap 2 around the user's waist.

Figure 6:
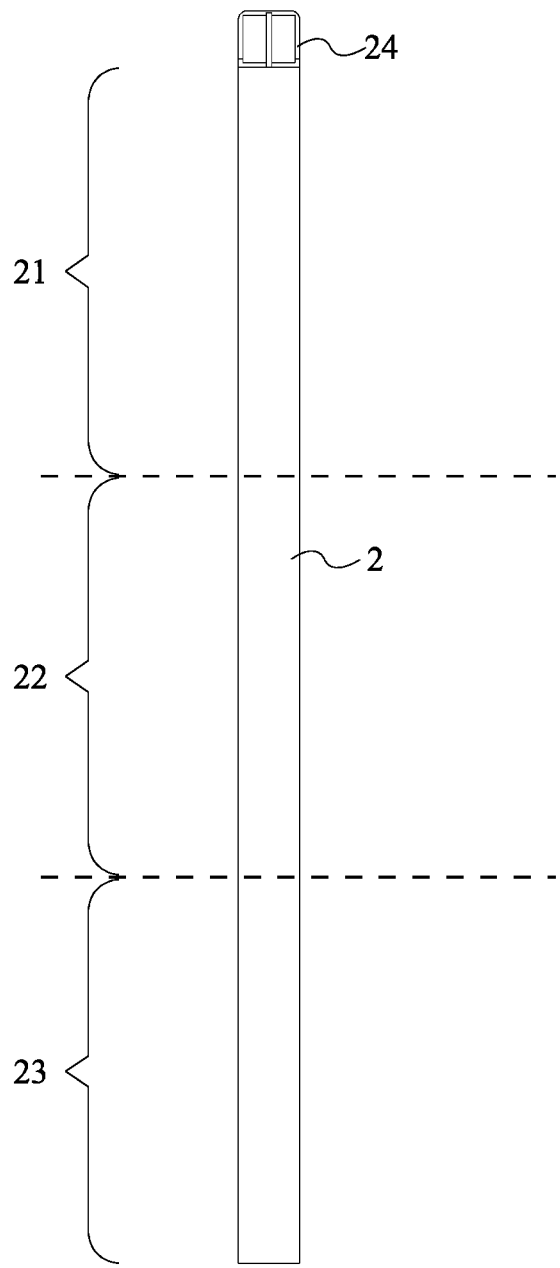
FIG. 6 is a top view of a single length-adjustable strap present invention.
Figure 7:
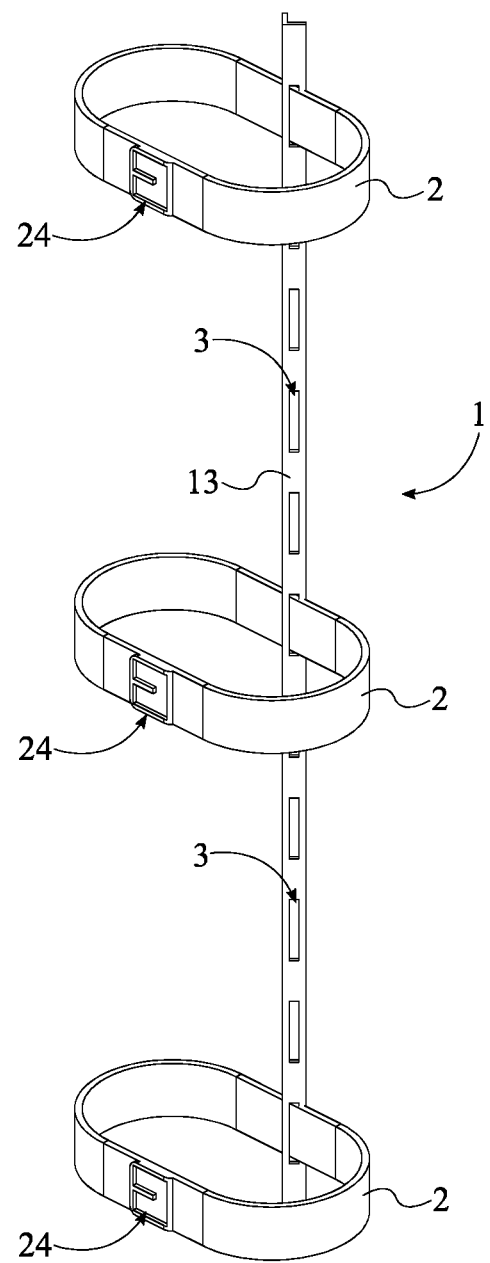
FIG. 7 is a perspective view of an embodiment of the present invention where the support rod is a V-shaped bar.
Figure 8:
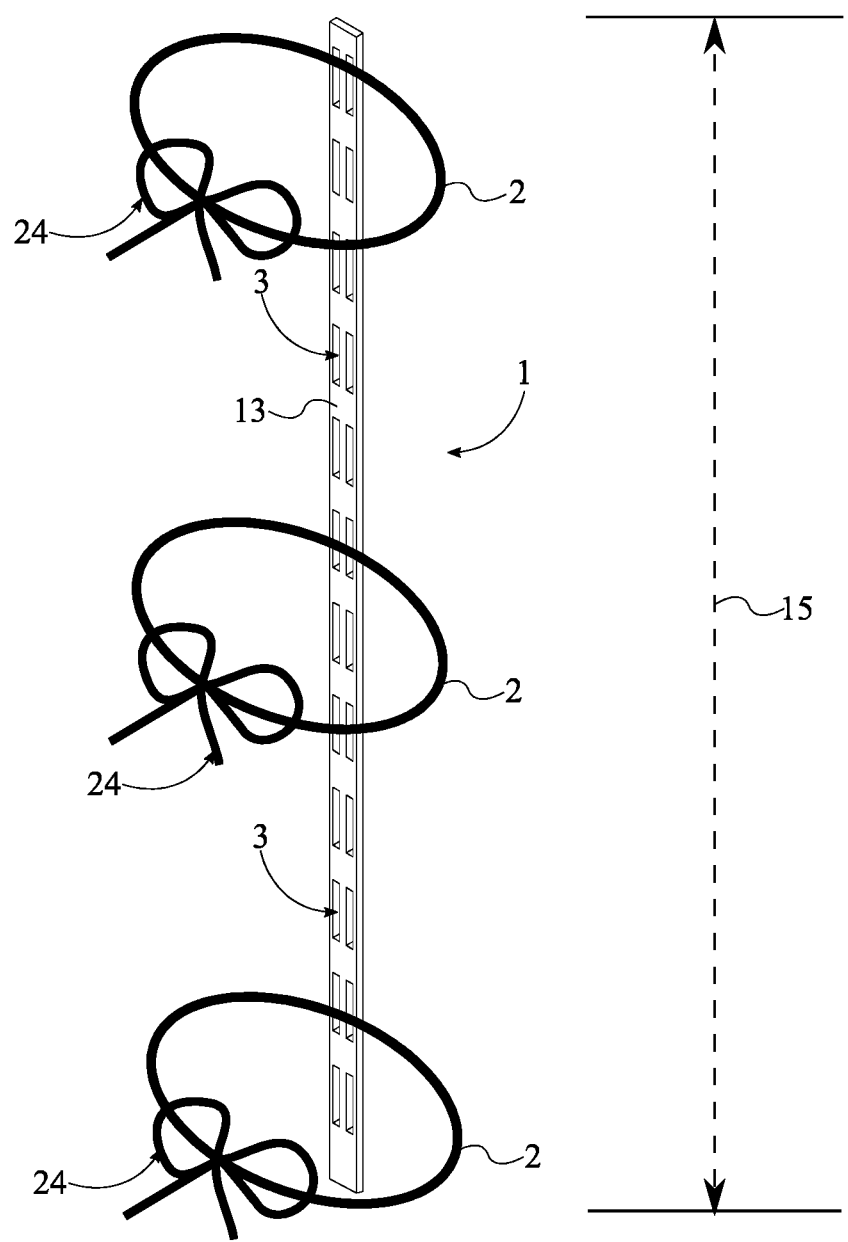
FIG. 8 is a perspective view of an embodiment of the present invention where the first end portion and the second end portion of the length-adjustable strap are knotted together.

As can be seen in FIG. 1 and FIG. 6, through FIG. 8, the present invention is designed to be affixed to the user's body by a wide variety of straps. To that end, each of the plurality of length-adjustable straps 2 comprises a first end portion 21, a central portion 22, a second end portion 23, and an adjustable fastener 24. The first end portion 21, the central portion 22 and the second end portion 23 identify sections of the length-adjustable strap 2. As such, the central portion 22 is positioned in between the first end portion 21 and the second end portion 23. Consequently, the first end portion 21 and the second end portion 23 form the terminal ends of the adjustable-length strap. The adjustable fastener 24 is a fastening mechanism that is designed to close the loop of a belt or strap. The adjustable fastener 24 can be, but is not limited to, a belt buckle, a quick-release fastener, or a hook and loop mechanism. In the preferred embodiment of the present invention, the first end portion 21 and the second end portion 23 are attached to each other by the adjustable fastener 24 so that the user is able to easily attach and detach the two ends of the length-adjustable strap. In a third alternative embodiment of the present invention, the first end portion 21 and the second end portion 23 are knotted to each other. As a result, the user is able to employ rope as the length-adjustable strap. In a fourth alternative embodiment of the present invention, the support rod is a V-shaped beam.

Although the invention has been explained in relation to its preferred embodiment, it is to be understood that many other possible modifications and variations can be made without departing from the spirit and scope of the invention as hereinafter claimed.

What is claimed is:
1. An apparatus for fixing bad posture comprising:
a support rod;
a plurality of length-adjustable straps;
a plurality of strap-attachment points;
the support rod comprising a rod body, a mounting face and a bracing face;
the mounting face and the bracing face being laterally positioned along the rod body;
the mounting face and the bracing face being positioned opposite to each other about the rod body;
the plurality of strap-attachment points being serially distributed along the rod body;
the rod body comprising a pair of bars;
the rod body being of V-shaped by the pair of bars being connected with each other and being oriented with each other via an acute angle, an obtuse angle or a right angle;
each of the plurality of strap-attachment points comprising a pair of slots, a corresponding slot among the pair of slots traversing through a corresponding bar among the pair of bars from the mounting face to the bracing face, the pair of slots being positioned offset from each other, each of the pair of slots being oriented parallel to a length of the support rod;
each of the plurality of length-adjustable straps being engaged to a corresponding point from a plurality of selected points, wherein the plurality of selected points are from the plurality of strap-attachment points;
each of plurality of length-adjustable straps traversing through each of the pair of slots of the corresponding point;
each of the plurality of length-adjustable straps comprising a first end portion, a central portion, a second end portion and an adjustable fastener;
the central portion being positioned in between the first end portion and the second end portion; and
the first end portion and the second end portion being attached to each other by the adjustable fastener.
2. The apparatus for fixing bad posture as claimed in claim 1 comprising:
a padding material; and
the padding material being superimposed onto the bracing face.
3. The apparatus for fixing bad posture as claimed in claim 1 comprising:

the plurality of selected points comprising a head-proximal point, a chest-proximal point, and a waist-proximal point;

the chest-proximal point being positioned offset from the head-proximal point along the support rod; and the waist-proximal point being positioned offset from the chest-proximal point along the support rod, opposite to the head-proximal point.

* * * * *